Figure 1:
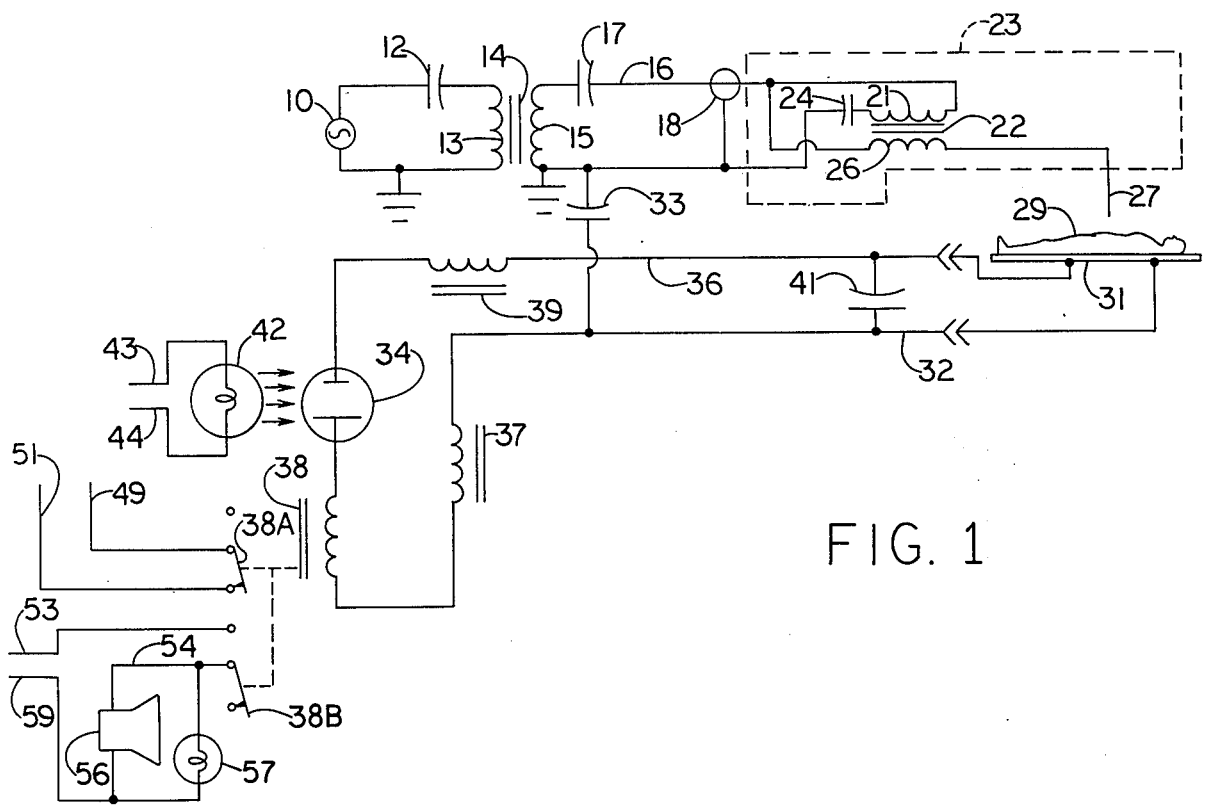

United States Patent [19]
Gonser

[11] 4,121,590
[45] Oct. 24, 1978

[54] SYSTEM FOR MONITORING INTEGRITY OF A PATIENT RETURN CIRCUIT

[75] Inventor: Donald I. Gonser, York, Pa.

[73] Assignee: Dentsply Research and Development Corporation, Milford, Del.

[21] Appl. No.: 777,330

[22] Filed: Mar. 14, 1977

[51] Int. Cl.² ............................................. A61N 3/00
[52] U.S. Cl. .............................. 128/303.13; 307/326; 323/9; 328/7
[58] Field of Search ..................... 128/303.13, 303.14, 128/303.17, 303.18, 2.1 P; 307/326; 323/9; 328/7

[56] References Cited
U.S. PATENT DOCUMENTS

| 3,601,126 | 8/1971 | Estes | 128/303.14 |
| 3,683,923 | 8/1972 | Anderson | 128/303.14 |
| 3,933,157 | 1/1976 | Bjurwill et al. | 128/303.14 |
| 3,958,175 | 5/1976 | Braun | 323/9 |
| 3,986,495 | 10/1976 | Miller | 128/2.1 P |

FOREIGN PATENT DOCUMENTS 1,139,927  11/1962  Fed. Rep. of Germany ...... 128/303.13

Primary Examiner—Lee S. Cohen
Attorney, Agent, or Firm—James W. Pearce; Roy F. Schaeperklaus

[57] ABSTRACT

A monitor for a patient return circuit of a radiofrequency electrosurgical device in which an interrogation or measurement circuit is powered by a photovoltaic cell. Characteristics of the photovoltaic cell can limit the interrogation or measurement current to a value considered to be safe to a patient.

11 Claims, 2 Drawing Figures

SYSTEM FOR MONITORING INTEGRITY OF A PATIENT RETURN CIRCUIT

This invention relates to electrosurgical devices. More particularly, this invention relates to a device for monitoring the integrity of a patient return circuit of an electrosurgical device.

In the use of radiofrequency electrosurgical devices, it is essential that a passive electrode and return lead be intact to prevent radiofrequency burn danger to a patient or to operating room personnel. It has been a common practice to use an interrogation or measurement current to demonstrate that the intended return circuit is intact. However, if excessive interrogation or measurement currents reach the patient through the interrogation or measurement circuit, such excessive interrogation or measurement current can be lethal or can permanently injure the patient, particularly in a failure mode circumstance.

A secondary circuit failure mode problem exists in some present day electrosurgical equipment where, in the failure mode situation, sizable shock or even lethal currents can be passed through a patient to ground from a return lead interrogation or measurement current secondary circuit source.

It is an object of this invention to provide a system which inherently limits the direct current voltage available to circulate in radiofrequency return leads in both a normally operating mode and circuit failure mode which could occur.

A further object of this invention is to provide a passive electrode and return lead monitoring circuit for a radiofrequency electrosurgical device which provides an interrogation or measurement current which cannot exceed a fixed value.

A further object of this invention is to provide such a monitoring circuit in which power circuits of a radiofrequency electrosurgical generator supply power to the monitoring circuit but are fully isolated therefrom.

Briefly, this invention provides a monitoring circuit for a passive electrode and return lead of a radiofrequency electrosurgical device in which an interrogation or measurement current is provided by a photovoltaic cell. The photovoltaic cell can be powered by a radiating source or lamp which, in turn, can be powered by an appropriate electrical power source. The electrical power source can be a portion of circuitry of a radiofrequency generator of the electrosurgical device. The power circuits of the radiofrequency generator are fully isolated from the photovoltaic cell because there is no direct connection therebetween. The voltage and current supplied by the photovoltaic cell to the monitoring circuit is limited by the electrical characteristics of the photovoltaic cell and inherently cannot exceed a given output voltage at optical saturation of the photovoltaic cell. The output voltage of the photovoltaic cell at optical saturation can be sufficiently low that there is limited potential danger to the patient even in a failure mode circumstance. The interrogation or measurement current can be used to actuate a sensing means such as a relay or the like in the monitoring circuit. The relay can actuate an alarm and can act to disable the radiofrequency generator in the event of failure of integrity of the passive electrode and intended return circuit.

Figure 2:
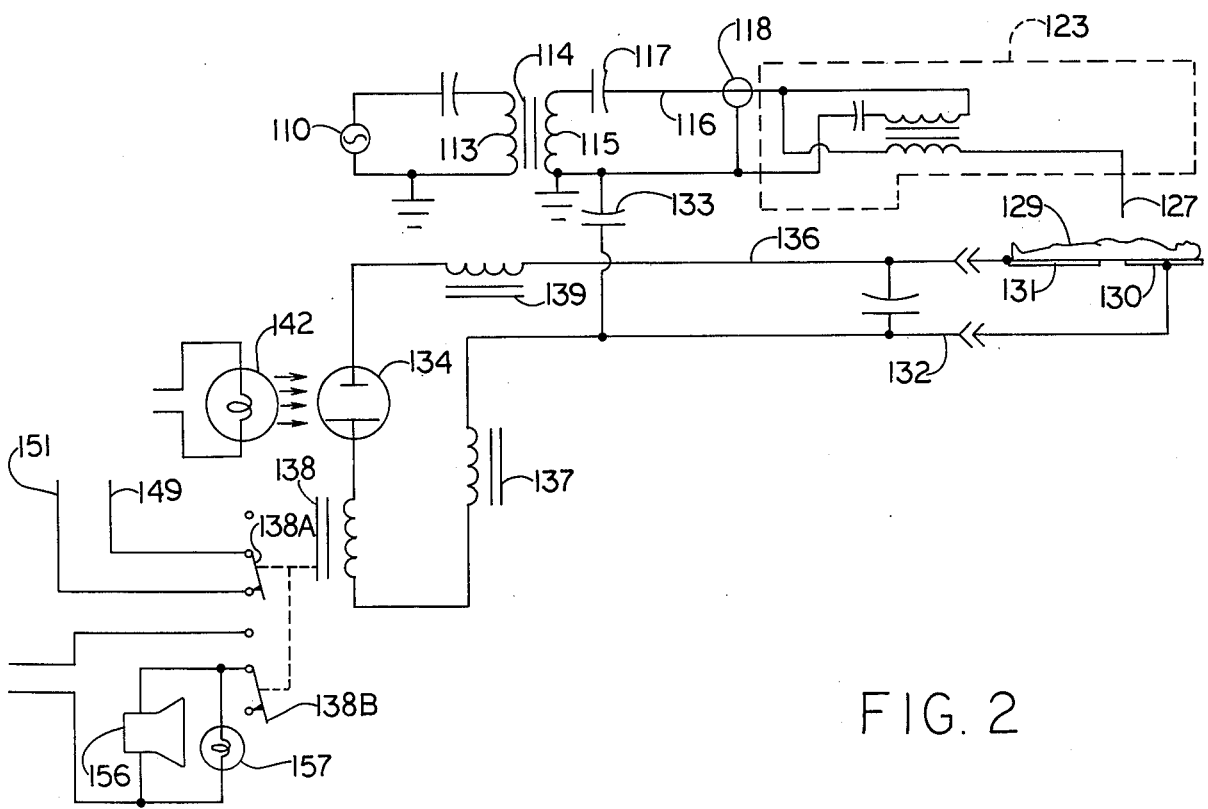

The above and other objects and features of the invention will be apparent to those skilled in the art to which this invention pertains from the following detailed description and the drawings, in which:

FIG. 1 is a schematic circuit diagram showing a device for monitoring the integrity of a patient return circuit for an electrosurgical device constructed in accordance with an embodiment of this invention; and FIG. 2 is a schematic circuit diagram showing a device for monitoring the integrity of a patient return circuit for an electrosurgical device constructed in accordance with another embodiment of this invention.

In the following detailed description and the drawings, like reference characters indicate like parts.

In FIG. 1 is shown a circuit for a radiofrequency electrosurgical device having a patient return monitoring circuit constructed in accordance with an embodiment of this invention. The device includes a radiofrequency generator 10 coupled through a condenser 12 to a primary winding 13 of a coupling transformer 14. One side of a secondary winding 15 of the coupling transformer 14 is coupled to a power lead 16 through a condenser 17. The power lead 16 is the inner or shielded conductor of a coaxial cable 18. The outer conductor or shield of the coaxial cable 18 is connected to ground as is the other side of the secondary winding 16 of the coupling transformer 14. The power lead 16 is connected to one end of a primary winding 21 of a handpiece transformer 22, which is mounted in a handpiece 23. The other end of the primary winding 21 is coupled to the shield of the coaxial cable 18 through a capacitor 24. A secondary winding 26 of the handpiece transformer 22 powers an active electrode 27. One end of the secondary winding 26 is connected to the active electrode, and the other end of the secondary winding 26 is connected to the power lead 16.

Return from a patient 29 is provided through a passive electrode 31 and a return lead 32, which is connected to the passive electrode and is coupled to ground through a coupling condenser 33. An interrogation or monitoring current is provided by a photovoltaic cell 34, which is coupled to the return lead 32 and to an interrogation or monitoring lead 36, which is also connected to the passive electrode 31. The photovoltaic cell 34 is coupled to the return lead 32 through a radiofrequency inductor 37 and through the coil of a relay 38 and to the interrogation or monitoring lead 36 through a radiofrequency inductor 39. The inductors 37 and 39 prevent radiofrequency return current from circulating through the photovoltaic cell and through the sensitive coil of the relay 38. A capacitor 41 is connected between the return lead 32 and the interrogation or monitoring lead 36 to carry radiofrequency current to the output winding coupling capacitor 33 should there be a break in the return lead 32.

The photovoltaic cell 34 can be illuminated by an appropriate lamp 42, which can be powered by leads 43 and 44. The leads 43 and 44 can be connected to an appropriate portion of the circuitry of the radiofrequency generator 10, not shown in detail, to provide the necessary voltage to operate the lamp 42. As long as the monitoring circuit including the return lead 32, the interrogation or monitoring lead 36, the photovoltaic cell 34 and the coil of the relay 38 is unbroken and the lamp 42 is illuminated, relay poles 38A and 38B are held in the position shown. The pole 38A connects leads 49 and 51, which can be a part of the circuitry of the radiofrequency generator which must be connected to permit the radiofrequency generator to power the coupling transformer 14 and the active electrode 27.

In the event of a break in the return lead 32, the relay 38 is de-energized, and the poles 38A and 38B swing to their other positions. Then the leads 49 and 51 are disconnected so that the radiofrequency generator is disabled to power the active electrode. In addition, the pole 38B connects a lead 53 to a lead 54. A warning horn 56 and a warning lamp 57 are connected between the lead 54 and a lead 59. The leads 53 and 59 can be connected to an appropriate portion of the circuitry of the radiofrequency generator to provide a voltage for operating the warning horn 56 and the warning lamp 57.

The photovoltaic cell 34 can be designed to have an output of 0.6 volts D.C. and a current of 60 milliamperes. Such a photovoltaic cell in open circuit, no load condition can have a limiting voltage of 0.8 volts D.C. Such a cell can operate a sensitive relay such as a Potter-Brumfield relay MDP-2109. The lamp 42 can be a low voltage annunciator incandescent tungsten filament lamp such as a Sylvania 6RB or 12RB annunciator lamp. Such a lamp, when operated at 50% of full output rating has a very long life and supplies sufficient radiant energy to optically saturate the photovoltaic cell.

In FIG. 2 is shown a circuit for a radiofrequency electrosurgical device which includes a patient return monitoring circuit constructed in accordance with another embodiment of this invention. The device of FIG. 2 includes a radiofrequency generator 110, which is coupled to a primary winding 113 of a coupling transformer 114. One side of a secondary winding 115 of the transformer is coupled through a condenser 117 to a power lead 116, which is the central or shielded conductor of a coaxial cable 118. The other side of the secondary winding and the outer conductor of the coaxial cable 118 are connected to ground. The coaxial cable powers an active electrode 127 carried by a handpiece 123 in the same manner as already described with reference to the first form of monitoring circuit. Return from a patient 129 is provided through a first passive In FIG. 2 is shown a circuit for a radiofrequency electrosurgical device which includes a patient return monitoring circuit constructed in accordance with another embodiment of this invention. The device of FIG. 2 includes a radiofrequency generator 110, which is coupled to a primary winding 113 of a coupling transformer 114. One side of a secondary winding 115 of the transformer is coupled through a condenser 117 to a power lead 116, which is the central or shielded conductor of a coaxial cable 118. The other side of the secondary winding and the outer conductor of the coaxial cable 118 are connected to ground. The coaxial cable powers an active electrode 127 carried by a handpiece 123 in the same manner as already described with reference to the first form of monitoring circuit. Return from a patient 129 is provided through a first passive electrode section 130 and a second passive electrode section 131. A return lead 132 is connected to the passive electrode section 130. A monitoring or measurement lead 136 is connected to the passive electrode section 131. The return lead 132 is coupled to ground through a coupling capacitor 133. A photovoltaic cell 134 supplies a monitoring or measurement current through a circuit including a radiofrequency inductor 139, a monitoring or measurement lead 136, the passive electrode section 131, the patient 129, the passive electrode section 130, the return lead 132, a radiofrequency inductor 137, and a coil of a relay 138. As long as a lamp 142 illuminates the photovoltaic cell 134, the patient is in good electrical contact with both of the passive electrode sections 130 and 131, and the return lead 132 and the monitoring or measurement lead 136 are intact so that the monitoring circuit is complete, the relay 138 is energized, and a pole 138A connects leads 149 and 151. The leads 149 and 151 can be part of the circuitry of the radiofrequency generator 110 (not shown in detail) which must be connected to permit the radiofrequency generator to power the coupling transformer 114 and the active electrode 127. However, if the patient does not have good electrical contact with one of the passive electrode sections 130 and 131, or if there is a break in the return lead 132 or in the monitoring or measurement lead 136, the poles of the relay 138 swing to their other position at which the leads 149 and 151 are not connected and a pole 138B forms a connection which energizes a horn 156 and a warning lamp 157 in the same manner as described with relation to the first form of monitoring circuit. The maximum magnitude of the monitoring or measurement current which passes through the patient 129 is limited by the characteristics of the photovoltaic cell to a value sufficiently low that there is substantially no danger to the patient.

The circuits for monitoring a patient return circuit illustrated in the drawings and described above are subject to modification without departing from the spirit and scope of the appended claims.

Having described my invention, what I claim as new and desire to secure by letters patent is:

1. A system for monitoring the integrity of a patient intended return of a radiofrequency electrosurgical device including a passive electrode and a return lead means attached to the passive electrode, said system comprising a monitoring circuit including said passive electrode, said return lead means, a photovoltaic cell, and current sensing means, said passive electrode, said return lead means, said photovoltaic cell, and said current sensing means being connected in series, means for illuminating the photovoltaic cell, and means actuated by the current sensing means for indicating a discontinuity in the monitering circuit, the voltage in the monitoring circuit being limited by the limiting voltage of the photovoltaic cell.

2. A system as in claim 1 wherein the monitoring circuit includes radiofrequency inductance means isolating the photovoltaic cell and the current sensing means from the passive electrode and the return lead means.

3. A system as in claim 1 wherein the monitoring circuit includes a second return lead means connected to the passive electrode, the passive electrode, the second return lead means, the return lead means, the photovoltaic cell, and the current sensing means are connected in series, the return lead means is coupled to ground, and capacitor means couples the second return lead means and the return lead means.

4. A system as in claim 3 wherein the passive electrode includes two sections, the return lead means is connected to one of the sections, and the second return lead means is connected to the other section.

5. The combination of a radiofrequency electrosurgical device which includes a radiofrequency generator, an active electrode, means actuated by the radiofrequency generator for supplying radiofrequency current to the active electrode, a passive electrode and a return lead means attached to the passive electrode for returning radiofrequency current to the generator with a monitoring circuit including said passive electrode, said return lead means, a photovoltaic cell, and current sensing means, said passive electrode, said return lead means, said photovoltaic cell, and said current sensing means being connected in series, means for illuminating the photovoltaic cell, means actuated by the current sensing means for indicating a discontinuity in the monitoring circuit, and means activated by the current sensing means to disable the radiofrequency generator from supplying radiofrequency current to the active electrode when indicating the discontinuity, the voltage in the monitoring circuit being limited by the limiting voltage of the photovoltaic cell.

6. The combination of a radiofrequency electrosurgical device which includes a radiofrequency generator, an active electrode, means actuated by the radiofrequency generator for supplying radiofrequency current to the active electrode, a passive electrode and a return lead means attached to the passive electrode returning radiofrequency current to the generator with a monitoring circuit including said passive electrode, said return lead means, a photovoltaic cell, and current sensing means, said passive electrode, said return lead means, said photovoltaic cell, and said current sensing means being connected in series, means for illuminating the photovoltaic cell, means actuated by the current sensing means for indicating a discontinuity in the monitoring circuit, a warning device and means activated by the current sensing means to activate the warning device when indicating the discontinuity, the voltage in the monitoring circuit being limited by the limiting voltage of the photovoltaic cell.

7. A system for monitoring the integrity of a patient return of a radiofrequency electrosurgical device which includes a passive electrode including a pair of sections, a first return lead means connected to one of said sections, a second return lead means connected to the other of said sections, a photovoltaic cell and a current sensing means connected in series between the first return lead means and the second return lead means, means for illuminating the photovoltaic cell, and means actuated by the current sensing means for indicating a discontinuity in the lead means, the voltage in the monitoring system being limited by the limiting voltage of the photovoltaic cell.

8. A system as in claim 7 which includes radiofrequency inductance means isolating the photovoltaic cell and the current sensing means from the passive electrode sections, the first return lead means and the second return lead means.

9. A system as in claim 7 which includes capacitor means coupling the first return lead means and the second return lead means.

10. The combination of a radiofrequency electrosurgical device which includes a radiofrequency generator, an active electrode, means actuated by the radiofrequency generator for supplying radiofrequency current to the active electrode, a passive electrode including a pair of sections, a first return lead means connected to one of said sections, and a second return lead means connected to the other of said sections, said lead means for returning radiofrequency current to the generator with a monitoring circuit which includes the passive electrode, the first return lead means, the second return lead means, a photovoltaic cell and a current sensing means, the photovoltaic cell and the current sensing means being connected in series between the first return lead means and the second return lead means, means for illuminating the photovoltaic cell, means actuated by the current sensing means for indicating a discontinuity in the lead means, and means activated by the current sensing means to disable the radiofrequency generator from supplying radiofrequency current to the active electrode when indicating the discontinuity, the voltage in the monitoring circuit being limited by the limiting voltage of the photovoltaic cell.

11. The combination of a radiofrequency electrosurgical device which includes a radiofrequency generator, an active electrode, means actuated by the radiofrequency generator for supplying radiofrequency current to the active electrode, a passive electrode including a pair of sections, a first return lead means connected to one of said sections, and a second return lead means connected to the other of said sections, said lead means for returning radiofrequency current to the generator, with a monitoring circuit which includes the passive electrode, the first return lead means, the second return lead means, a photovoltaic cell and a current sensing means, the photovoltaic cell and the current sensing means being connected in series between the first return lead means and the second return lead means, means for illuminating the photovoltaic cell, means actuated by the current sensing means for indicating a discontinuity in the lead means, a warning device, and means activated by the current sensing means to activate the warning device when indicating the discontinuity, the voltage in the monitoring circuit being limited by the limiting voltage of the photovoltaic cell.

* * * * *

UNITED STATES PATENT OFFICE
CERTIFICATE OF CORRECTION

Patent No. 4,121,590         Dated   October 24, 1978

Inventor(s)   DONALD I. GONSER

It is certified that error appears in the above-identified patent and that said Letters Patent are hereby corrected as shown below:

Column 6, line 12, after "generator" insert a comma.

Signed and Sealed this

Thirtieth Day of January 1979

[SEAL]

Attest:

RUTH C. MASON
Attesting Officer

DONALD W. BANNER
Commissioner of Patents and Trademarks